(12) United States Patent
McDermott (10) Patent No.: US 12,318,528 B2
(45) Date of Patent: Jun. 3, 2025

(54) VARIABLE ORIFICE FISTULA GRAFT

(71) Applicant: MOZARC MEDICAL US LLC, Minneapolis, MN (US)

(72) Inventor: Sean McDermott, Weymouth, MA (US)

(73) Assignee: MOZARC MEDICAL US LLC, Minneapolis, MN (US)

(*) Notice: Subject to any disclaimer, the term of this patent is extended or adjusted under 35 U.S.C. 154(b) by 41 days.

(21) Appl. No.: 17/458,696

(22) Filed: Aug. 27, 2021

(65) Prior Publication Data

US 2022/0133974 A1    May 5, 2022

Related U.S. Application Data

(60) Provisional application No. 63/107,547, filed on Oct. 30, 2020.

(51) Int. Cl.
    *A61M 1/36*    (2006.01)
    *A61L 31/04*   (2006.01)
    *A61L 31/14*   (2006.01)

(52) U.S. Cl.
    CPC ......... *A61M 1/3655* (2013.01); *A61L 31/041* (2013.01); *A61L 31/148* (2013.01); *A61M 1/3661* (2014.02); *A61M 2205/10* (2013.01)

(58) Field of Classification Search
    CPC ............ A61B 2017/1135; A61B 17/11; A61B 17/12131; A61B 17/12036; A61B 2017/1107; A61B 17/12022–1204; A61M 1/3655; A61M 1/3661; A61M 1/3653; A61M 2205/3331; A61F 2/06; G03B 9/06–10; F15D 1/0005; Y10T 137/4666; Y10T 137/7746
    See application file for complete search history.

(56) References Cited

U.S. PATENT DOCUMENTS

| | | | |
|---|---|---|---|
| 5,662,711 A * | 9/1997 | Douglas | A61F 2/06 604/9 |
| 5,951,870 A | 9/1999 | Utterberg | |
| 6,019,788 A * | 2/2000 | Butters | A61F 2/064 604/8 |
| 6,044,691 A | 4/2000 | Kenley et al. | |
| 6,066,261 A | 5/2000 | Spickermann | |
| 6,077,443 A | 6/2000 | Goldau | |
| 6,106,776 A | 8/2000 | Borovetz et al. | |

(Continued)

FOREIGN PATENT DOCUMENTS

| WO | WO-2015025912 A1 * | 2/2015 | ............ A61M 1/029 |
| WO | WO-2019243155 A1 * | 12/2019 | ........... A61B 17/132 |
| WO | 2021161176 A1 | 8/2021 | |

OTHER PUBLICATIONS

Extended European Search Report issued in corresponding application EP 21205680.8 dated Feb. 28, 2022 (10 pages).

*Primary Examiner* — Philip R Wiest
*Assistant Examiner* — Linnae E. Raymond (57) ABSTRACT

A medical implant includes a primary tubular member having a first end and a second end and defining a primary longitudinal axis and a primary lumen. The primary tubular member is disposed in an arterial-venous connection. The medical implant also includes a baffle disposed transversely to the primary longitudinal axis within the primary lumen. The baffle defines at least one aperture therethrough.

20 Claims, 4 Drawing Sheets

(56) References Cited

U.S. PATENT DOCUMENTS

| | | |
|---|---|---|
| 6,114,466 A | 9/2000 | Davankov et al. |
| 6,126,831 A | 10/2000 | Goldau et al. |
| 6,133,393 A | 10/2000 | Davankov et al. |
| 6,138,517 A | 10/2000 | Laursen et al. |
| 6,159,377 A | 12/2000 | Davankov et al. |
| 6,200,289 B1 | 3/2001 | Hochman et al. |
| 6,217,826 B1 | 4/2001 | Reeder et al. |
| 6,221,040 B1 | 4/2001 | Kleinekofort |
| 6,228,262 B1 | 5/2001 | Shin et al. |
| 6,241,945 B1 | 6/2001 | Owen |
| 6,248,087 B1 | 6/2001 | Spears et al. |
| 6,306,346 B1 | 10/2001 | Lindsay |
| 6,325,774 B1 | 12/2001 | Bene et al. |
| 6,344,139 B1 | 2/2002 | Utterberg |
| 6,348,152 B1 | 2/2002 | Kawahara et al. |
| 6,387,324 B1 | 5/2002 | Patterson et al. |
| 6,395,180 B2 | 5/2002 | Chioini et al. |
| 6,409,024 B1 | 6/2002 | Nakashima et al. |
| 6,432,309 B1 | 8/2002 | Fuke et al. |
| 6,468,427 B1 | 10/2002 | Frey |
| 6,500,151 B1 | 12/2002 | Cobb et al. |
| 6,503,451 B2 | 1/2003 | Ikeda et al. |
| 6,519,569 B1 | 2/2003 | White et al. |
| 6,526,357 B1 | 2/2003 | Soussan et al. |
| 6,537,240 B2 | 3/2003 | Cavicchioli et al. |
| 6,555,059 B1 | 4/2003 | Myrick et al. |
| 6,572,576 B2 | 6/2003 | Brugger et al. |
| 6,576,191 B1 | 6/2003 | Myrick et al. |
| 6,582,387 B2 | 6/2003 | Derek et al. |
| 6,582,811 B1 | 6/2003 | Davankov et al. |
| 6,585,675 B1 | 7/2003 | O'Mahony et al. |
| 6,592,551 B1 | 7/2003 | Cobb |
| 6,595,942 B2 | 7/2003 | Kleinekofort |
| 6,601,432 B1 | 8/2003 | Ericson et al. |
| 6,602,424 B1 | 8/2003 | Kramer et al. |
| 6,602,468 B2 | 8/2003 | Patterson et al. |
| 6,605,218 B2 | 8/2003 | Kozawa et al. |
| 6,607,697 B1 | 8/2003 | Muller |
| 6,613,280 B2 | 9/2003 | Myrick et al. |
| 6,622,542 B2 | 9/2003 | Derek et al. |
| 6,623,443 B1 | 9/2003 | Polaschegg |
| 6,626,355 B2 | 9/2003 | Sasse et al. |
| 6,627,164 B1 | 9/2003 | Wong |
| 6,632,359 B1 | 10/2003 | Uezumi et al. |
| 6,638,710 B2 | 10/2003 | Leinenbach et al. |
| 6,640,611 B2 | 11/2003 | Ericson et al. |
| 6,648,845 B1 | 11/2003 | Gotch et al. |
| 6,653,841 B1 | 11/2003 | Koerdt et al. |
| 6,673,314 B1 | 1/2004 | Burbank et al. |
| 6,676,621 B1 | 1/2004 | Menninger |
| 6,682,698 B2 | 1/2004 | Chambers et al. |
| 6,685,450 B2 | 2/2004 | Bandis et al. |
| 6,689,083 B1 | 2/2004 | Gelfand et al. |
| 6,691,040 B2 | 2/2004 | Bosetto et al. |
| 6,691,047 B1 | 2/2004 | Fredericks |
| 6,712,978 B2 | 3/2004 | Leinenbach et al. |
| 6,723,284 B1 | 4/2004 | Reeder et al. |
| 6,726,647 B1 | 4/2004 | Sternby et al. |
| 6,730,266 B2 | 5/2004 | Matson et al. |
| 6,738,052 B1 | 5/2004 | Manke et al. |
| 6,759,008 B1 | 7/2004 | Patterson et al. |
| 6,767,333 B1 | 7/2004 | Muller et al. |
| 6,773,412 B2 | 8/2004 | O'Mahony et al. |
| 6,775,577 B2 | 8/2004 | Crnkovich et al. |
| 6,786,885 B2 | 9/2004 | Hochman et al. |
| 6,796,955 B2 | 9/2004 | O'Mahony et al. |
| 6,804,991 B2 | 10/2004 | Balschat et al. |
| 6,811,707 B2 | 11/2004 | Rovatti et al. |
| 6,811,750 B2 | 11/2004 | Patterson et al. |
| 6,818,196 B2 | 11/2004 | Wong |
| 6,821,432 B2 | 11/2004 | Metzner |
| 6,830,693 B2 | 12/2004 | Govoni et al. |
| 6,843,099 B2 | 1/2005 | Derek et al. |
| 6,846,161 B2 | 1/2005 | Kline et al. |
| 6,849,235 B2 | 2/2005 | Myrick et al. |
| 6,854,620 B2 | 2/2005 | Ramey |
| 6,855,291 B2 | 2/2005 | Patterson et al. |
| 6,860,866 B1 | 3/2005 | Graf et al. |
| 6,861,266 B1 | 3/2005 | Sternby |
| 6,868,309 B1 | 3/2005 | Begelman |
| 6,877,713 B1 | 4/2005 | Gray et al. |
| 6,880,034 B2 | 4/2005 | Manke et al. |
| 6,881,344 B2 | 4/2005 | Vasta et al. |
| 6,887,216 B2 | 5/2005 | Hochman et al. |
| 6,890,315 B1 | 5/2005 | Levin et al. |
| 6,890,482 B2 | 5/2005 | Divino, Jr. et al. |
| 6,899,847 B2 | 5/2005 | Myrick et al. |
| 6,908,546 B2 | 6/2005 | Smith |
| 6,917,828 B2 | 7/2005 | Fukuda |
| 6,923,782 B2 | 8/2005 | O'Mahony et al. |
| 6,929,619 B2 | 8/2005 | Fago et al. |
| 6,929,751 B2 | 8/2005 | Bowman, Jr. et al. |
| 6,935,560 B2 | 8/2005 | Andreasson et al. |
| 6,936,221 B1 | 8/2005 | Divino, Jr. et al. |
| 6,936,222 B2 | 8/2005 | Mortensen et al. |
| 6,939,111 B2 | 9/2005 | Huitt et al. |
| 6,939,468 B2 | 9/2005 | Wang et al. |
| 6,945,954 B2 | 9/2005 | Hochman et al. |
| 6,949,214 B2 | 9/2005 | Frey |
| 6,952,963 B2 | 10/2005 | Delnevo |
| 6,960,328 B2 | 11/2005 | Bortun et al. |
| 6,966,979 B2 | 11/2005 | Pedrazzi |
| 6,994,811 B2 | 2/2006 | Kools |
| 7,001,353 B2 | 2/2006 | Bosetto et al. |
| 7,004,924 B1 | 2/2006 | Brugger et al. |
| 7,011,761 B2 | 3/2006 | Muller |
| 7,013,727 B2 | 3/2006 | Delnevo |
| 7,014,765 B2 | 3/2006 | Dannenmaier |
| 7,022,284 B2 | 4/2006 | Brian et al. |
| 7,025,226 B2 | 4/2006 | Ramey |
| 7,033,498 B2 | 4/2006 | Wong |
| 7,033,539 B2 | 4/2006 | Krensky et al. |
| 7,072,710 B2 | 7/2006 | Chamney |
| 7,077,819 B1 | 7/2006 | Goldau et al. |
| 7,077,956 B2 | 7/2006 | Rovatti |
| 7,087,033 B2 | 8/2006 | Brugger et al. |
| 7,087,168 B2 | 8/2006 | Oishi et al. |
| 7,087,269 B2 | 8/2006 | Lee et al. |
| 7,097,630 B2 | 8/2006 | Gotch et al. |
| 7,125,493 B2 | 10/2006 | Wang et al. |
| 7,131,956 B1 | 11/2006 | Pirazzoli et al. |
| 7,131,957 B2 | 11/2006 | Muller et al. |
| 7,135,156 B2 | 11/2006 | Hai et al. |
| 7,140,542 B2 | 11/2006 | Andreasson et al. |
| 7,147,616 B2 | 12/2006 | Pedrazzi et al. |
| 7,153,285 B2 | 12/2006 | Lauman et al. |
| 7,154,378 B1 | 12/2006 | Ertas et al. |
| 7,166,084 B2 | 1/2007 | Utterberg |
| 7,169,352 B1 | 1/2007 | Felt et al. |
| 7,170,591 B2 | 1/2007 | Ohishi et al. |
| 7,172,569 B2 | 2/2007 | Kleinekofort |
| 7,172,570 B2 | 2/2007 | Cavalcanti et al. |
| 7,175,081 B2 | 2/2007 | Andreasson et al. |
| 7,175,809 B2 | 2/2007 | Gelfand et al. |
| 7,182,256 B2 | 2/2007 | Andreasson et al. |
| 7,186,342 B2 | 3/2007 | Pirazzoli et al. |
| 7,186,420 B2 | 3/2007 | Chang et al. |
| 7,186,966 B2 | 3/2007 | Al-Ali |
| 7,232,424 B2 | 6/2007 | Boyne-Aitken |
| 7,241,272 B2 | 7/2007 | Karoor et al. |
| 7,252,767 B2 | 8/2007 | Bortun et al. |
| 7,258,914 B2 | 8/2007 | Morikawa et al. |
| 7,299,981 B2 | 11/2007 | Hickle et al. |
| 7,303,540 B2 | 12/2007 | O'Mahony et al. |
| 7,311,689 B2 | 12/2007 | Levin et al. |
| 7,341,568 B2 | 3/2008 | Zhang |
| 7,347,837 B2 | 3/2008 | Azzolini |
| 7,381,195 B2 | 6/2008 | Mori et al. |
| 7,393,337 B2 | 7/2008 | Tonelli et al. |
| 7,399,289 B2 | 7/2008 | Gelfand et al. |
| 7,420,660 B2 | 9/2008 | Muller |
| 7,422,570 B2 | 9/2008 | Gerlach et al. |
| 7,442,302 B2 | 10/2008 | Mabuchi et al. |
| 7,462,161 B2 | 12/2008 | O'Mahony et al. |

(56) References Cited

U.S. PATENT DOCUMENTS

| | | |
|---|---|---|
| 7,488,447 B2 | 2/2009 | Sternby |
| 7,494,590 B2 | 2/2009 | Felding et al. |
| 7,540,851 B2 | 6/2009 | O'Mahony et al. |
| 7,563,240 B2 | 7/2009 | Gross et al. |
| 7,563,376 B2 | 7/2009 | Oishi |
| 7,566,432 B2 | 7/2009 | Wong |
| 7,575,562 B2 | 8/2009 | Oishi et al. |
| 7,585,286 B2 | 9/2009 | O'Mahony et al. |
| 7,592,184 B2 | 9/2009 | Khalil et al. |
| 7,608,060 B2 | 10/2009 | Gillespie, Jr. et al. |
| 7,615,158 B2 | 11/2009 | Sternby et al. |
| 7,622,043 B2 | 11/2009 | Sawada et al. |
| 7,635,349 B2 | 12/2009 | Tribe et al. |
| 7,638,052 B2 | 12/2009 | Mabuchi et al. |
| 7,639,136 B1 | 12/2009 | Wass et al. |
| 7,648,474 B2 | 1/2010 | Paolini et al. |
| 7,648,476 B2 | 1/2010 | Bock et al. |
| 7,648,477 B2 | 1/2010 | Vinci et al. |
| 7,661,293 B2 | 2/2010 | Dam |
| 7,694,565 B2 | 4/2010 | Koerdt et al. |
| 7,699,992 B2 | 4/2010 | Sternby |
| 7,731,689 B2 | 6/2010 | Prisco et al. |
| 7,736,507 B2 | 6/2010 | Wong |
| 7,748,275 B2 | 7/2010 | Kouda et al. |
| 7,749,184 B2 | 7/2010 | Cavalcanti et al. |
| 7,749,435 B2 | 7/2010 | Ogihara et al. |
| 7,751,043 B2 | 7/2010 | Scarpaci et al. |
| 7,758,532 B2 | 7/2010 | Mori et al. |
| 7,766,863 B2 | 8/2010 | Gillespie, Jr. et al. |
| 7,771,379 B2 | 8/2010 | Treu |
| 7,776,219 B2 | 8/2010 | Brugger et al. |
| 7,780,618 B2 | 8/2010 | Felt et al. |
| 7,790,113 B2 | 9/2010 | Putnam et al. |
| 7,794,419 B2 | 9/2010 | Paolini et al. |
| 7,815,809 B2 | 10/2010 | Jansson et al. |
| 7,823,287 B2 | 11/2010 | Gerlach et al. |
| 7,824,354 B2 | 11/2010 | Vinci et al. |
| 7,837,042 B2 | 11/2010 | Yokota et al. |
| 7,854,726 B2 | 12/2010 | Fago et al. |
| 7,857,976 B2 | 12/2010 | Bissler et al. |
| 7,862,530 B2 | 1/2011 | Callan et al. |
| 7,878,783 B2 | 2/2011 | Kunz |
| 7,896,842 B2 | 3/2011 | Palmroos et al. |
| 7,905,853 B2 | 3/2011 | Chapman et al. |
| 7,905,855 B2 | 3/2011 | Childers |
| 7,906,093 B2 | 3/2011 | Wong |
| 7,911,353 B2 | 3/2011 | Bedingfield |
| 7,922,007 B2 | 4/2011 | Mabuchi et al. |
| 7,922,899 B2 | 4/2011 | Vasta et al. |
| 7,935,071 B2 | 5/2011 | Levin et al. |
| 7,935,072 B2 | 5/2011 | Tonelli et al. |
| 7,938,792 B2 | 5/2011 | Roger et al. |
| 7,938,967 B2 | 5/2011 | Folden et al. |
| 7,955,289 B2 | 6/2011 | O'Mahony et al. |
| 7,955,291 B2 | 6/2011 | Sternby |
| 7,959,196 B2 | 6/2011 | Dale |
| 7,959,808 B2 | 6/2011 | Yeager et al. |
| 7,967,769 B2 | 6/2011 | Faul et al. |
| 7,981,280 B2 | 7/2011 | Carr et al. |
| 7,985,196 B2 | 7/2011 | Kopperschmidt et al. |
| 7,988,768 B2 | 8/2011 | Yardimci et al. |
| 7,988,854 B2 | 8/2011 | Tsukamoto |
| 7,990,272 B2 | 8/2011 | Wass et al. |
| 7,993,297 B2 | 8/2011 | Vinci et al. |
| 8,012,114 B2 | 9/2011 | Daniel et al. |
| 8,034,161 B2 | 10/2011 | Gura et al. |
| 8,035,517 B2 | 10/2011 | Gibson |
| 8,038,886 B2 | 10/2011 | Folden et al. |
| 8,043,076 B2 | 10/2011 | Kopperschmidt |
| 8,051,991 B2 | 11/2011 | Krause et al. |
| 8,066,658 B2 | 11/2011 | Karoor et al. |
| 8,070,707 B2 | 12/2011 | Gelfand et al. |
| 8,075,509 B2 | 12/2011 | Molducci et al. |
| 8,078,333 B2 | 12/2011 | Kienman et al. |
| 8,080,161 B2 | 12/2011 | Ding et al. |
| 8,087,702 B2 | 1/2012 | Schmidt |
| 8,088,090 B2 | 1/2012 | Felt et al. |
| 8,091,407 B2 | 1/2012 | Schneider et al. |
| 8,095,390 B2 | 1/2012 | Bluemler et al. |
| 8,104,348 B2 | 1/2012 | Balschat et al. |
| 8,104,624 B2 | 1/2012 | Chidambaran et al. |
| 8,105,260 B2 | 1/2012 | Tonelli et al. |
| 8,111,159 B2 | 2/2012 | Andreasson et al. |
| 8,136,675 B2 | 3/2012 | Buck et al. |
| 8,137,553 B2 | 3/2012 | Fulkerson et al. |
| 8,140,274 B2 | 3/2012 | Gagel et al. |
| 8,178,040 B2 | 5/2012 | Brauer |
| 8,182,691 B2 | 5/2012 | Stahl |
| 8,197,432 B2 | 6/2012 | O'Mahony et al. |
| 8,197,745 B1 | 6/2012 | Buck et al. |
| 8,202,428 B2 | 6/2012 | Heilmann et al. |
| 8,202,503 B2 | 6/2012 | Putnam et al. |
| 8,210,049 B2 | 7/2012 | Brugger |
| 8,219,982 B2 | 7/2012 | Harkanyi et al. |
| 8,220,643 B2 | 7/2012 | Eisen |
| 8,240,636 B2 | 8/2012 | Smith |
| 8,246,564 B2 | 8/2012 | Myrick et al. |
| 8,287,736 B2 | 10/2012 | Roncadi et al. |
| 8,298,427 B2 | 10/2012 | Ficheux et al. |
| 8,314,740 B2 | 11/2012 | Blumberg, Jr. |
| 8,315,654 B2 | 11/2012 | Balschat et al. |
| 8,315,885 B2 | 11/2012 | Krogh et al. |
| 8,317,168 B2 | 11/2012 | Murakami |
| 8,317,499 B2 | 11/2012 | Ibragimov |
| 8,317,738 B2 | 11/2012 | Ishida et al. |
| 8,325,045 B2 | 12/2012 | Dattolo et al. |
| 8,328,749 B2 | 12/2012 | Murakami et al. |
| 8,333,724 B2 | 12/2012 | Barrett et al. |
| 8,343,085 B2 | 1/2013 | Toyoda et al. |
| 8,350,195 B2 | 1/2013 | Hedmann et al. |
| 8,353,870 B2 | 1/2013 | Levin et al. |
| 8,361,023 B2 | 1/2013 | Bedingfield |
| 8,394,046 B2 | 3/2013 | Nuernberger et al. |
| 8,394,321 B2 | 3/2013 | Franzoni et al. |
| 8,398,858 B2 | 3/2013 | Kashefi-Khorasani et al. |
| 8,400,298 B2 | 3/2013 | Rada |
| 8,409,445 B2 | 4/2013 | Levin et al. |
| 8,409,502 B2 | 4/2013 | Mortensen et al. |
| 8,409,864 B2 | 4/2013 | Ash |
| 8,425,767 B2 | 4/2013 | Fava et al. |
| 8,430,834 B2 | 4/2013 | Kopperschmidt |
| 8,432,547 B2 | 4/2013 | Scarpaci et al. |
| 8,449,487 B2 | 5/2013 | Hovland et al. |
| 8,459,543 B2 | 6/2013 | Devergne et al. |
| 8,465,446 B2 | 6/2013 | Chapman et al. |
| 8,480,609 B2 | 7/2013 | Fava et al. |
| 8,485,998 B2 | 7/2013 | Moll et al. |
| 8,486,021 B2 | 7/2013 | Hoshide et al. |
| 8,496,824 B2 | 7/2013 | Remkes et al. |
| 8,496,874 B2 | 7/2013 | Gellman et al. |
| 8,497,107 B2 | 7/2013 | Merchant |
| 8,512,271 B2 | 8/2013 | Moissl et al. |
| 8,512,554 B2 | 8/2013 | Yu et al. |
| 8,512,564 B2 | 8/2013 | Bene et al. |
| 8,518,247 B2 | 8/2013 | Akita et al. |
| 8,518,326 B2 | 8/2013 | Brady et al. |
| 8,529,491 B2 | 9/2013 | Beiriger |
| 8,539,573 B2 | 9/2013 | Newlin et al. |
| 8,545,425 B2 | 10/2013 | Lundtveit et al. |
| 8,551,032 B2 * | 10/2013 | Faul ............... A61B 17/11 604/8 |
| 8,558,964 B2 | 10/2013 | Bedingfield |
| 8,560,510 B2 | 10/2013 | Brueggerhoff et al. |
| 8,562,834 B2 | 10/2013 | Kamen et al. |
| 8,562,876 B2 | 10/2013 | Sternberg |
| 8,568,595 B2 | 10/2013 | Castellarnau |
| 8,574,309 B2 | 11/2013 | Galea et al. |
| 8,585,907 B2 | 11/2013 | Raiford et al. |
| 8,585,968 B2 | 11/2013 | Morley et al. |
| 8,596,467 B2 | 12/2013 | Krause et al. |
| 8,597,190 B2 | 12/2013 | Rule et al. |
| 8,597,227 B2 | 12/2013 | Childers et al. |
| 8,597,505 B2 | 12/2013 | Fulkerson et al. |
| 8,603,021 B2 | 12/2013 | Levin et al. |

(56) References Cited

U.S. PATENT DOCUMENTS

| | | |
|---|---|---|
| 8,608,658 B2 | 12/2013 | Burbank et al. |
| 8,609,022 B2 | 12/2013 | Nakao et al. |
| 8,610,577 B2 | 12/2013 | Blumberg, Jr. |
| 8,617,393 B2 | 12/2013 | Remkes et al. |
| 8,625,100 B2 | 1/2014 | Hanko |
| 8,640,887 B2 | 2/2014 | Wong |
| 8,641,615 B2 | 2/2014 | Burbank et al. |
| 8,641,655 B2 | 2/2014 | Rambod et al. |
| 8,647,410 B2 | 2/2014 | Borenstein et al. |
| 8,657,775 B2 | 2/2014 | Hutchison et al. |
| 8,663,372 B2 | 3/2014 | Romdhane et al. |
| 8,672,145 B2 | 3/2014 | Eisen |
| 8,679,348 B2 | 3/2014 | Burbank et al. |
| 8,684,927 B2 | 4/2014 | Basaglia |
| 8,685,320 B2 | 4/2014 | Ogihara et al. |
| 8,687,003 B2 | 4/2014 | Dalesch et al. |
| 8,733,559 B2 | 5/2014 | Wong |
| 8,741,147 B2 | 6/2014 | Bene et al. |
| 8,747,342 B2 | 6/2014 | Caleffi et al. |
| 8,747,742 B2 | 6/2014 | Kawamura et al. |
| 8,748,538 B2 | 6/2014 | Krause et al. |
| 8,764,981 B2 | 7/2014 | Ding et al. |
| 8,764,987 B2 | 7/2014 | Gross et al. |
| 8,769,625 B2 | 7/2014 | Wang et al. |
| 8,771,215 B2 | 7/2014 | Tonelli et al. |
| 8,771,516 B2 | 7/2014 | Krause et al. |
| 8,775,196 B2 | 7/2014 | Simpson et al. |
| 8,784,668 B2 | 7/2014 | Beiriger |
| 8,803,044 B2 | 8/2014 | Kienman et al. |
| 8,813,769 B2 | 8/2014 | Gastauer et al. |
| 8,814,830 B2 | 8/2014 | Morris et al. |
| 8,828,225 B2 | 9/2014 | Okafuji et al. |
| 8,836,519 B2 | 9/2014 | Wright et al. |
| 8,845,571 B2 | 9/2014 | Kotanko et al. |
| 8,858,486 B2 | 10/2014 | Zhang et al. |
| 8,858,792 B2 | 10/2014 | Ding et al. |
| 8,864,700 B2 | 10/2014 | Kawamura et al. |
| 8,870,812 B2 | 10/2014 | Alberti et al. |
| 8,881,600 B2 | 11/2014 | Puppini et al. |
| 8,881,915 B2 | 11/2014 | Yokota et al. |
| 8,882,696 B2 | 11/2014 | Tamari |
| 8,882,704 B2 | 11/2014 | Fago et al. |
| 8,883,066 B2 | 11/2014 | Shiki |
| 8,900,173 B2 | 12/2014 | Sugioka |
| 8,905,959 B2 | 12/2014 | Basaglia |
| 8,906,240 B2 | 12/2014 | Crnkovich et al. |
| 8,906,300 B2 | 12/2014 | Wang et al. |
| 8,911,629 B2 | 12/2014 | Tsukamoto |
| 8,924,458 B2 | 12/2014 | Levin et al. |
| 8,926,544 B2 | 1/2015 | Hogard |
| 8,937,553 B2 | 1/2015 | Fujioka et al. |
| 8,950,241 B2 | 2/2015 | Hedmann et al. |
| 8,992,777 B2 | 3/2015 | Doyle |
| 9,005,153 B2 | 4/2015 | Kopperschmidt et al. |
| 9,022,981 B2 | 5/2015 | Oesterreich et al. |
| 9,028,740 B2 | 5/2015 | Gohl et al. |
| 9,033,908 B2 | 5/2015 | Schilthuizen et al. |
| 9,050,411 B2 | 6/2015 | Kelly et al. |
| 9,072,830 B2 | 7/2015 | Kelly et al. |
| 9,072,831 B2 | 7/2015 | Kelly et al. |
| 9,072,843 B2 | 7/2015 | Kelly et al. |
| 9,080,985 B2 | 7/2015 | Stevenson et al. |
| 9,095,661 B2 | 8/2015 | Bene |
| 9,117,012 B2 | 8/2015 | Basaglia |
| 9,119,949 B2 | 9/2015 | Brandl et al. |
| 9,140,251 B2 | 9/2015 | Beiriger |
| 9,155,825 B2 | 10/2015 | Kelly et al. |
| 9,161,980 B2 | 10/2015 | Emnebrant et al. |
| 9,162,020 B2 | 10/2015 | Vantard et al. |
| 9,165,112 B2 | 10/2015 | Doyle et al. |
| 9,173,988 B2 | 11/2015 | Barrett et al. |
| 9,174,172 B2 | 11/2015 | Shiki |
| 9,178,891 B2 | 11/2015 | Wang et al. |
| 9,180,238 B2 | 11/2015 | Bedingfield et al. |
| 9,187,744 B2 | 11/2015 | Merchant |
| 9,189,597 B2 | 11/2015 | Bluemler et al. |
| 9,199,023 B2 | 12/2015 | Takeuchi |
| 9,199,024 B2 | 12/2015 | Sasaki et al. |
| 9,199,205 B2 | 12/2015 | Weber et al. |
| 9,203,143 B2 | 12/2015 | Blumberg, Jr. |
| 9,205,247 B2 | 12/2015 | Ueda et al. |
| 9,208,296 B1 | 12/2015 | Romanick |
| 9,211,369 B2 | 12/2015 | Gartner et al. |
| 9,212,988 B2 | 12/2015 | Akita et al. |
| 9,215,985 B2 | 12/2015 | Gross et al. |
| 9,216,246 B2 | 12/2015 | Kelly et al. |
| 9,220,827 B2 | 12/2015 | Meibaum et al. |
| 9,220,832 B2 | 12/2015 | Weaver et al. |
| 9,226,999 B2 | 1/2016 | Nakel et al. |
| 9,234,302 B2 | 1/2016 | Weber et al. |
| 9,242,035 B2 | 1/2016 | Karoor |
| 9,242,036 B2 | 1/2016 | Bluchel et al. |
| 9,243,625 B2 | 1/2016 | Brandl et al. |
| 9,243,991 B2 | 1/2016 | Wagner et al. |
| 9,250,216 B2 | 2/2016 | Wright et al. |
| 9,254,279 B2 | 2/2016 | Karoor et al. |
| 9,267,500 B2 | 2/2016 | Gronau et al. |
| 9,270,010 B2 | 2/2016 | Blumberg, Jr. |
| 9,272,127 B2 | 3/2016 | Rada et al. |
| 9,278,168 B2 | 3/2016 | Gellman et al. |
| 9,283,246 B2 | 3/2016 | Fenn et al. |
| 9,283,310 B2 | 3/2016 | Royer et al. |
| 9,289,545 B2 | 3/2016 | Olde et al. |
| 9,293,110 B2 | 3/2016 | Dolgos et al. |
| 9,295,394 B2 | 3/2016 | Kopperschmidt et al. |
| 9,295,778 B2 | 3/2016 | Kamen et al. |
| 9,296,611 B2 | 3/2016 | Wong |
| 9,302,037 B2 | 4/2016 | Wilt et al. |
| 9,308,308 B2 | 4/2016 | Ding et al. |
| 9,310,232 B2 | 4/2016 | Heide et al. |
| 9,311,448 B2 | 4/2016 | Gruendken et al. |
| 9,314,207 B2 | 4/2016 | Marterstock |
| 9,314,480 B2 | 4/2016 | Jansson et al. |
| 9,314,560 B2 | 4/2016 | Wiktor |
| 9,320,845 B2 | 4/2016 | Falkenhagen et al. |
| 9,345,827 B2 | 5/2016 | Hertz |
| 9,352,083 B2 | 5/2016 | Heitmeiter et al. |
| 9,352,139 B2 | 5/2016 | Reiter et al. |
| 9,352,283 B2 | 5/2016 | Ying et al. |
| 9,353,220 B2 | 5/2016 | Savariar et al. |
| 9,354,640 B2 | 5/2016 | Byler |
| 9,360,129 B2 | 6/2016 | Smith |
| 9,364,597 B2 | 6/2016 | Wolff et al. |
| 9,364,602 B2 | 6/2016 | Kelly et al. |
| 9,364,604 B2 | 6/2016 | Ferrarini et al. |
| 9,370,614 B2 | 6/2016 | Ahrens |
| 9,375,524 B2 | 6/2016 | Levin et al. |
| 9,383,288 B2 | 7/2016 | Solem et al. |
| 9,387,441 B2 | 7/2016 | Ding et al. |
| 9,399,092 B2 | 7/2016 | Christmann |
| 9,400,199 B2 | 7/2016 | Wolff |
| 9,402,941 B2 | 8/2016 | Rambod et al. |
| 9,402,945 B2 | 8/2016 | Hogard et al. |
| 9,402,987 B2 | 8/2016 | Kamen et al. |
| 9,404,825 B2 | 8/2016 | Katz et al. |
| 9,408,958 B2 | 8/2016 | Wang et al. |
| 9,415,201 B2 | 8/2016 | Marterstock |
| 9,427,513 B2 | 8/2016 | Holmer et al. |
| 9,427,518 B2 | 8/2016 | Brueckner |
| 9,433,356 B2 | 9/2016 | Olde et al. |
| 9,435,459 B2 | 9/2016 | Bedingfield |
| 9,436,802 B2 | 9/2016 | Romanick |
| 9,440,198 B2 | 9/2016 | McCloskey et al. |
| 9,442,036 B2 | 9/2016 | Furmanski et al. |
| 9,452,252 B2 | 9/2016 | Kopperschmidt |
| 9,463,202 B2 | 10/2016 | Jansson et al. |
| 9,463,266 B2 | 10/2016 | Noguchi et al. |
| 9,470,341 B2 | 10/2016 | Brehm et al. |
| 9,474,846 B2 | 10/2016 | Steger |
| 9,488,510 B2 | 11/2016 | Beavis et al. |
| 9,492,794 B2 | 11/2016 | Yokota et al. |
| 9,504,778 B2 | 11/2016 | Hopping et al. |
| 9,514,322 B2 | 12/2016 | Golshenas |
| 9,514,518 B2 | 12/2016 | Gillespie et al. |

(56) References Cited

U.S. PATENT DOCUMENTS

| | | |
|---|---|---|
| 9,517,296 B2 | 12/2016 | Fulkerson et al. |
| 9,518,958 B2 | 12/2016 | Wilt et al. |
| 9,527,040 B2 | 12/2016 | Krause et al. |
| 9,527,627 B2 | 12/2016 | Eyrard et al. |
| 9,542,578 B2 | 1/2017 | Pattolo et al. |
| 9,545,469 B2 | 1/2017 | Curtis et al. |
| 9,548,533 B2 | 1/2017 | Blumberg, Jr. |
| 9,550,021 B2 | 1/2017 | Beden et al. |
| 9,555,146 B2 | 1/2017 | Fehr et al. |
| 9,555,181 B2 | 1/2017 | Hedmann et al. |
| 9,568,432 B2 | 2/2017 | Baxi et al. |
| 9,582,645 B2 | 2/2017 | Yu et al. |
| 9,585,992 B2 | 3/2017 | Bene |
| 9,599,599 B2 | 3/2017 | Ash et al. |
| 9,612,182 B2 | 4/2017 | Olde et al. |
| 9,616,160 B2 | 4/2017 | Daniel |
| 9,616,161 B2 | 4/2017 | Jansson et al. |
| 9,616,163 B2 | 4/2017 | Wong et al. |
| 9,616,164 B2 | 4/2017 | Nuernberger |
| 9,616,393 B2 | 4/2017 | Hidaka et al. |
| 9,635,111 B2 | 4/2017 | Wang et al. |
| 9,636,447 B2 | 5/2017 | Olde et al. |
| 9,642,961 B2 | 5/2017 | Kelly et al. |
| 9,655,922 B1 | 5/2017 | Jansson et al. |
| 9,662,485 B2 | 5/2017 | Chung et al. |
| 9,675,743 B2 | 6/2017 | Raiford et al. |
| 9,675,745 B2 | 6/2017 | Kelly et al. |
| 9,682,184 B2 | 6/2017 | Wong |
| 9,703,926 B2 | 7/2017 | Dolgos et al. |
| 9,707,329 B2 | 7/2017 | Merchant et al. |
| 9,713,670 B2 | 7/2017 | Herrmann et al. |
| 9,724,455 B2 | 8/2017 | Kopperschmidt et al. |
| 9,742,065 B2 | 8/2017 | Blumberg, Jr. |
| 9,744,300 B2 | 8/2017 | Kamen et al. |
| 9,750,865 B2 | 9/2017 | Vasta et al. |
| 9,752,730 B2 | 9/2017 | Voelz |
| 9,757,503 B2 | 9/2017 | Haecker et al. |
| 9,770,546 B2 | 9/2017 | Vasta |
| 9,775,937 B2 | 10/2017 | Wang et al. |
| 9,776,143 B2 | 10/2017 | Krause et al. |
| 9,782,528 B2 | 10/2017 | Balschat et al. |
| 9,791,270 B2 | 10/2017 | Paolini et al. |
| 9,795,731 B2 | 10/2017 | Kelly et al. |
| 9,795,932 B2 | 10/2017 | Yokota et al. |
| 9,802,162 B2 | 10/2017 | Hildwein et al. |
| 9,806,399 B2 | 10/2017 | Blumberg, Jr. |
| 9,808,586 B2 | 11/2017 | Kogan |
| 9,821,102 B2 | 11/2017 | Jansson et al. |
| 9,821,106 B1 | 11/2017 | Vasta et al. |
| 9,821,107 B2 | 11/2017 | Weaver et al. |
| 9,833,556 B2 | 12/2017 | Olde et al. |
| 9,836,185 B2 | 12/2017 | O'Mahony et al. |
| 9,844,620 B2 | 12/2017 | Stuva et al. |
| 9,846,085 B2 | 12/2017 | Newell et al. |
| 9,849,228 B2 | 12/2017 | Noack et al. |
| 9,855,380 B2 | 1/2018 | Ritter et al. |
| 9,878,086 B2 | 1/2018 | Kleinekofort |
| 9,883,799 B2 | 2/2018 | Kotanko et al. |
| 9,889,244 B2 | 2/2018 | Arrizza et al. |
| 9,901,669 B2 | 2/2018 | Wolff et al. |
| 9,901,726 B2 | 2/2018 | Stenzel et al. |
| 9,907,898 B2 | 3/2018 | Hedmann et al. |
| 9,921,271 B2 | 3/2018 | Labarthe et al. |
| 9,925,155 B2 | 3/2018 | Forsback et al. |
| 9,925,320 B2 | 3/2018 | Childers et al. |
| 9,933,391 B2 | 4/2018 | Hollstein |
| 9,950,104 B2 | 4/2018 | Gronau et al. |
| 9,974,895 B2 | 5/2018 | Storr et al. |
| 9,987,411 B2 | 6/2018 | Planas et al. |
| 9,993,777 B2 | 6/2018 | Hayashi et al. |
| 10,002,190 B2 | 6/2018 | West |
| 10,022,484 B2 | 7/2018 | Brugger et al. |
| 10,024,442 B2 | 7/2018 | Maenz et al. |
| 10,044,791 B2 | 8/2018 | Kamen et al. |
| 10,057,997 B2 | 8/2018 | Schafer et al. |
| 10,058,692 B2 | 8/2018 | Geiger et al. |
| 10,080,996 B2 | 9/2018 | Berzinis et al. |
| 10,099,000 B2 | 10/2018 | Strohhoefer et al. |
| 10,101,316 B2 | 10/2018 | Wolff et al. |
| 10,130,749 B2 | 11/2018 | Schade |
| 10,149,938 B2 | 12/2018 | Murphy et al. |
| 10,172,990 B2 | 1/2019 | Stenzel et al. |
| 10,188,991 B2 | 1/2019 | Menda et al. |
| 10,203,273 B2 | 2/2019 | Burkert |
| 10,247,663 B2 | 4/2019 | Janik et al. |
| 10,300,187 B2 | 5/2019 | Lisitschew |
| 10,307,531 B2 | 6/2019 | Faulhaber et al. |
| 10,322,220 B2 | 6/2019 | Riemenschneider |
| 10,391,228 B2 | 8/2019 | Kelly et al. |
| 10,716,572 B2 * | 7/2020 | Rolland ............ A61B 17/12036 |
| 11,564,690 B1 * | 1/2023 | Kellerman ....... A61B 17/12109 |
| 2004/0133147 A1 * | 7/2004 | Woo ...................... A61F 5/0079 |
| | | 604/9 |
| 2006/0155239 A1 | 7/2006 | Knudson et al. |
| 2009/0234431 A1 * | 9/2009 | Weinberger ................ A61F 2/06 |
| | | 623/1.13 |
| 2010/0286758 A1 * | 11/2010 | Berglund ................... A61F 2/91 |
| | | 623/1.15 |
| 2013/0274648 A1 * | 10/2013 | Weinberger ......... A61M 1/3655 |
| | | 604/9 |
| 2022/0054806 A1 * | 2/2022 | Kassab ............... A61M 60/841 |

\* cited by examiner

VARIABLE ORIFICE FISTULA GRAFT

CROSS-REFERENCE TO RELATED APPLICATIONS

The present application claims the benefit of and priority to U.S. Patent Provisional Application No. 63/107,547, filed on Oct. 30, 2020, the entire content of which is incorporated herein by reference.

BACKGROUND

When performing hemodialysis, a vascular access device functions as an access point through which blood is removed from the patient to be treated by a hemodialysis machine, and then returned to the patient. The vascular access lets large amounts of blood to flow during hemodialysis treatments to filter as much blood as possible per treatment. An arteriovenous ("AV") fistula is one type of vascular access and is a connection, made by a vascular surgeon, of an artery to a vein. An AV fistula causes added pressure and blood to flow into the vein causing the vein to remodel itself and grow larger and stronger thereby providing easy and reliable access. An AV graft uses a synthetic or a biologically derived tube, e.g., harvested vein, to interconnect an artery and a vein. In either of these procedures, once the connection is made, there is no tempering or controlling the arterial blood flow since the blood flow is immediately directed into the connected vessel. Thus, there is a need to provide for a medical implant that can regulate blood flow and pressure between interconnected artery and vein in AV fistulas and AV grafts.

SUMMARY

According to one embodiment of the present disclosure a medical implant for controlling blood flow is disclosed. The medical implant includes a primary tubular member having a first end and a second end and defining a primary longitudinal axis and a primary lumen. The primary tubular member is disposed in an arterial-venous connection. The medical implant also includes a baffle disposed transversely to the primary longitudinal axis within the primary lumen. The baffle defines at least one aperture therethrough.

Implementations of the above embodiment may include one or more of the following features. The arterial-venous connection may be an arterial-venous fistula with the medical implant interconnecting an artery and a vein. The primary tubular member and the secondary tubular member are transversely coupled to each other such that the first end of the primary tubular member is coupled to a side opening of the secondary tubular member. The arterial-venous connection may be an arterial-venous graft including a graft vessel interconnecting an artery and a vein. The primary tubular member is disposed within the graft vessel. The primary tubular member may be the graft vessel. The baffle may be formed from a biodegradable material configured to degrade over time thereby enlarging the at least one aperture. The biodegradable material may be a polymer selected from the group may include of polylactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid), polylactic acid, polyglycolic acid, polycaprolactone, fibrin, chitosan, polysaccharide, and combinations thereof. The baffle may be an electromechanical device configured to adjust at least one dimension of the at least one aperture. The primary tubular member may be a stent.

According to another embodiment of the present disclosure, a method of establishing an arterial-venous connection is disclosed. The method includes connecting a vein and an artery to form the arterial-venous connection. The method also includes inserting a medical implant into the arterial-venous connection. The medical implant includes a primary tubular member having a first end and a second end and defining a primary longitudinal axis and a primary lumen. The medical implant also includes a baffle disposed transversely to the primary longitudinal axis within the primary lumen, the baffle defining at least one aperture therethrough.

Implementations of the above embodiment may include one or more of the following features. The method where connecting the vein and the artery includes forming an arterial-venous fistula. Inserting the medical implant may include inserting the medical implant into the arterial-venous fistula. The medical implant may further include a secondary tubular member defining a secondary longitudinal axis and a secondary lumen, where the primary tubular member and the secondary tubular member are transversely coupled to each other such that the first end of the primary tubular member is coupled to a side opening of the secondary tubular member. Connecting the vein and the artery may include forming an arterial-venous graft having a graft vessel interconnecting an artery and a vein. Inserting the medical implant may include inserting the primary tubular member into the graft vessel. The primary tubular member is the graft vessel. The baffle may be formed from a biodegradable material configured to degrade over time thereby enlarging the at least one aperture. The biodegradable material may be a polymer selected from the group may include of polylactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid), polylactic acid, polyglycolic acid, polycaprolactone, fibrin, chitosan, polysaccharide, and combinations thereof. The baffle may be an electromechanical device configured to adjust at least one dimension of the at least one aperture. The primary tubular member may be a stent.

BRIEF DESCRIPTION OF THE DRAWINGS

Embodiments of the present disclosure are described herein with reference to the accompanying drawings, wherein.

DETAILED DESCRIPTION

Embodiments of the disclosed medical implants and methods are described in detail with reference to the drawings, in which like reference numerals designate identical or corresponding elements in each of the several views. As used herein the term "distal" refers to that portion of the medical implant, or component thereof, farther from the user, while the term "proximal" refers to that portion of the medical implant, or component thereof, closer to the user.

As used herein, the terms "biodegradable" and "bioabsorbable" are used with respect to a property of a material. "Biodegradable" is a material that is capable of being decomposed or broken down in vivo and subsequently excreted. "Bioabsorbable" is a material that is capable of being decomposed or broken down in vivo and subsequently resorbed. Both biodegradable and bioabsorbable materials are suitable for purposes of this application and thus for simplicity, unless otherwise directed, biodegradable materials and bioabsorbable materials are collectively referred to as "biodegradable" herein. Conversely, "non-biodegradable" is a biocompatible (i.e., not harmful to living tissue) material is not decomposed or broken down in vivo. In addition, the term "dissolution" as used in the description refers to the breakdown of both biodegradable and bioabsorbable materials.

As used herein, the terms parallel and perpendicular are understood to include relative configurations that are substantially parallel and substantially perpendicular up to about + or −5 degrees from true parallel and true perpendicular.

As will be described in detail below, a method of forming an arterial-venous connection such as an arteriovenous ("AV") fistula or an AV graft utilizing a medical implant disposed within a portion of the arterial-venous connection. The tubular member may be a tube having a baffle defining one or more apertures therethrough. The baffle may be formed from a biodegradable material such that the aperture enlarges overtime to allow for additional blood flow. This allows for the connected vessels to strengthen and to accommodate increased blood flow. In embodiments, the baffle may be a mechanical device configured to adjust the size of the aperture(s) in response to user controls.

Figure 1:
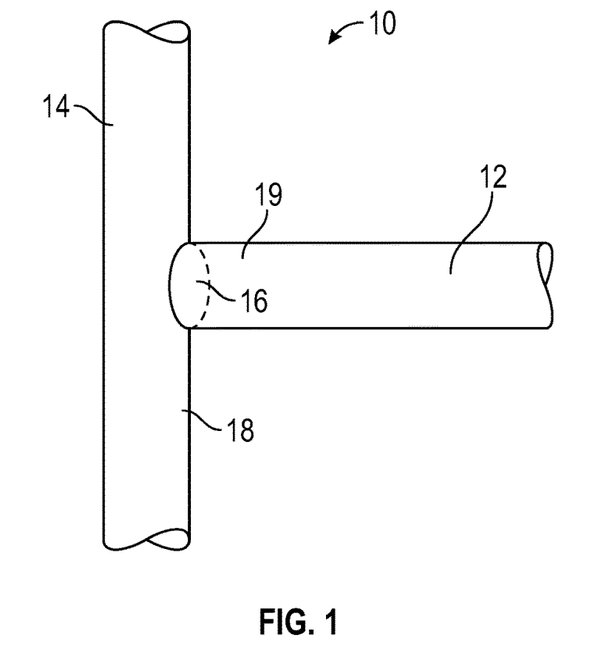
FIG. 1 is a side, schematic view of an AV fistula for forming a vein-artery connection according to an embodiment of the present disclosure.

FIG. 1 illustrates an AV fistula 10 according to the present disclosure. The AV fistula 10 is formed by making a fluid connection between a vein 12 and an artery 14. In particular, an anastomosis 16 is formed in a side 18 of the artery 14 and an end 19 of the vein 12 is connected to the side 18 of the artery 14 at the anastomosis 16.

Figure 2:
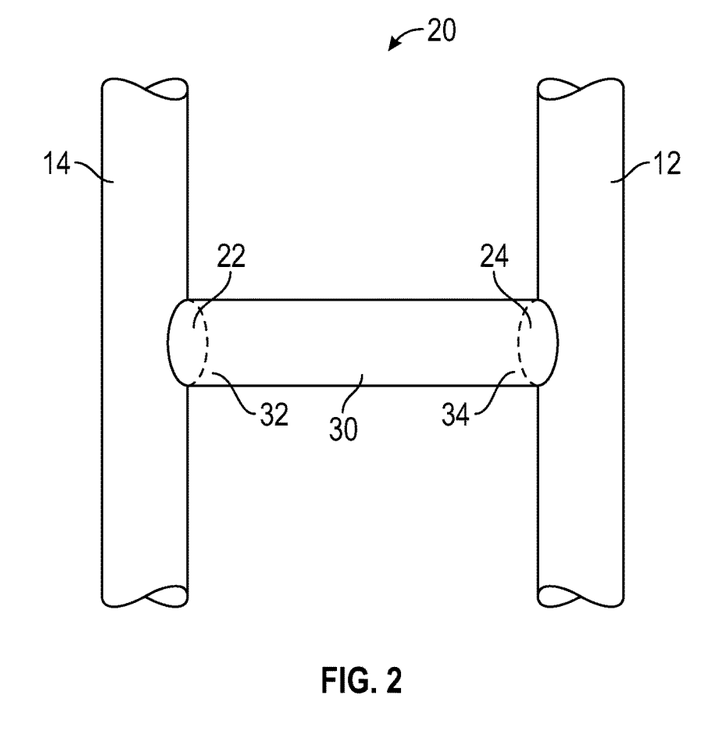
FIG. 2 is a side, schematic view of an AV graft for forming a vein-artery connection according to another embodiment of the present disclosure.

FIG. 2 shows an AV graft 20 according to the present disclosure. Similar to the AV fistula 10, the vein 12 and the artery 14 are fluidly coupled to each other, except rather than by a direct connection, an AV graft 20 is coupled to each of the vein 12 and the artery 14. A first anastomosis 22 is formed in the vein 12 and a second anastomosis 24 is formed in the artery 14. A graft vessel 30, which may be a harvested or an artificial blood vessel, having a first end 32 and a second end 34 which are coupled to each of the first anastomosis 22 and the second anastomosis 24, respectively.

Figure 3:
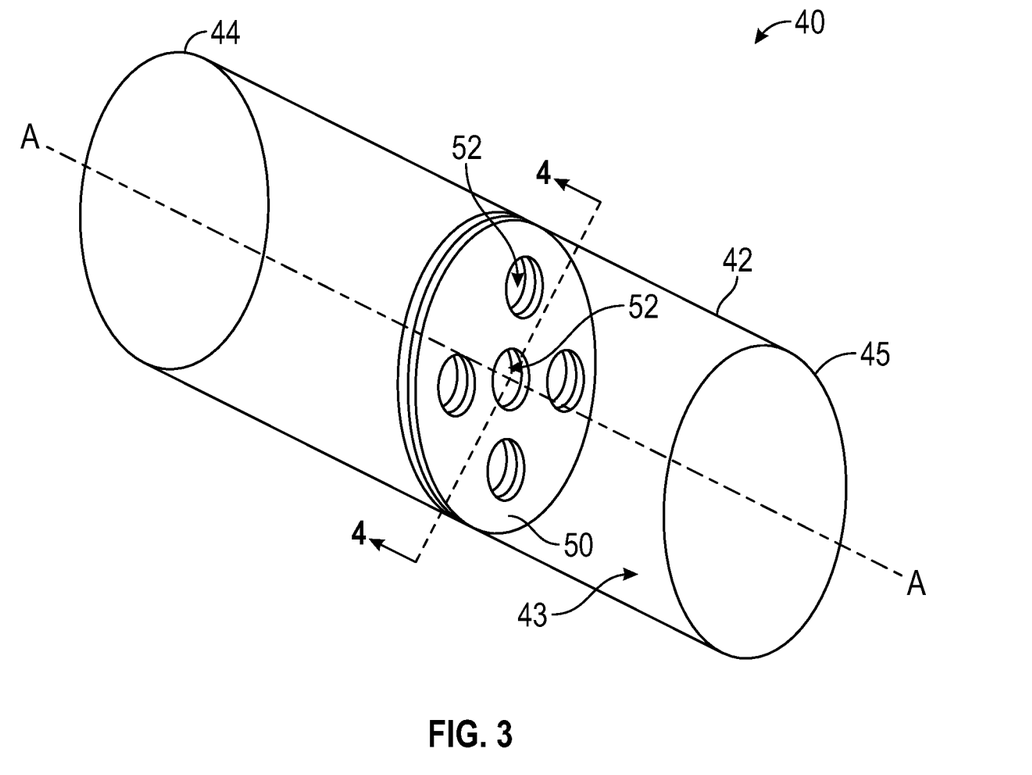
FIG. 3 is a perspective view of a medical implant for forming the AV graft of FIG. 2 according to an embodiment of the present disclosure.

With reference to FIG. 3 a medical implant 40 for use with the AV graft 20 is shown. The medical implant 40 is inserted into the grafted vessel 30. The medical implant 40 includes a tubular member 42 defining a longitudinal axis "A-A" and a lumen 43 therethrough. The tubular member 42 includes a proximal end portion 44 and a distal end portion 45. The tubular member 42 may be a stent having a lattice member formed from any suitable non-biodegradable material, such as metal or a shape memory material, such as a nickel-titanium alloy (nitinol) or shape memory polymers. The tubular member 42 may be machined or laser cut from a solid tube of material to form the interconnected filaments according to the present disclosure. In other embodiments, the tubular member 42 may be formed by braiding metal wire, polymer filaments, or combinations thereof, into desired shapes. In further embodiments, the tubular member 42 may be a self-expanding stent configured to apply outward radial force on the blood vessel.

The medical implant 40 also includes a baffle 50 that is securely coupled to the tubular member 42 and defining an aperture 52 therethrough. In certain embodiments, the baffle 50 may include a plurality of apertures 52 disposed in any suitable pattern, i.e., around the periphery of the baffle 50. The baffle 50 may be coupled to the tubular member 42 using adhesives or mechanical fasteners, such as sutures, and the like. The baffle 50 is substantially transverse to the longitudinal axis "A-A" such that blood flows only the through aperture 52.

The baffle 50 may be formed from a bioabsorbable/biodegradable material that dissolves or breaks down once exposed to blood. Suitable biodegradable materials include synthetic and naturally derived polymers and co-polymers, as well as blends, composites, and combinations thereof. Examples of suitable materials include but are not limited to polylactide (PLA) [poly-L-lactide (PLLA), poly-DL-lactide (PDLLA)], polyglycolide (PLG or PLGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) or two or more polymerizable monomers such as trimethylene carbonate, ε-caprolactone, polyethylene glycol, 4-tert-butyl caprolactone, N-acetyl caprolactone, poly(ethylene glycol)bis(carboxymethyl) ether, polylactic acid, polyglycolic acid, polycaprolactone, fibrin, chitosan, polysaccharides, and combinations thereof. In embodiments, the baffle 50 may be formed from a conformable material, such that where the tubular member 42 is a self-expanding stent, the baffle 50 is configured to form into a blocking configuration.

Since the baffle 50 is formed from a biodegradable material, over time the baffle 50 degrades. Due to degradation, the baffle 50 loses mass and volume, which also increases the size of the aperture 52. This allows for increased blood flow over time through the tubular member 42. The gradual change in the blood flow allows for remodeling of the vein 12 and increases maturation rate of the AV graft 20. In embodiments, the tubular member 42 may also be formed from a biodegradable material, similar to the baffle 50, such that after a predetermined period of time the medical implant 40 is fully resorbed leaving the AV graft 20 unobstructed. In further embodiments, the baffle 50 may be coupled directly to the graft vessel 30. Thus, the graft vessel 30 be manufactured with the baffle 50 being disposed therein such that the graft vessel 30 is used as the tubular member 42.

Figure 4:
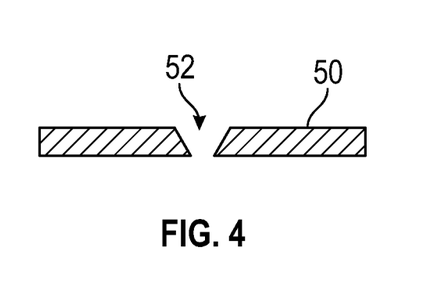
FIG. 4 is a cross-sectional view of a biodegradable baffle taken across a cross-sectional line 4-4 according to one embodiment for use with the medical implants according to the present disclosure.
Figure 5:
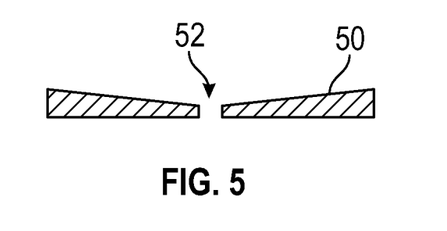
FIG. 5 is a cross-sectional view of a biodegradable baffle taken across a cross-sectional line 4-4 according to another embodiment for use with the medical implants according to the present disclosure.

With reference to FIGS. 3-5, the baffle 50 may have a disk-like shape having a diameter from about 2 mm to about 10 mm and a thickness from about 0.5 mm to about 3 mm. The thickness of the baffle 50 may be the same as shown in FIG. 4 or may vary as shown in FIG. 5. In particular, the thickness may decrease from the outer circumference of the baffle 50 (i.e., the edge contacting the tubular member 42) to the aperture 52. The aperture 52 may be disposed at the center of the baffle 50. The aperture 52 may have an initial diameter (i.e., prior to implantation) from about 5% to about 80% of the diameter of the baffle 50. In embodiments, the initial diameter of the aperture may be from about 0.1 mm to about 8 mm. The aperture 52 may have a frustoconical shape as shown in FIG. 4 with a wider opening facing the direction of the blood flow, i.e., facing the artery 14. In further embodiments, the aperture 52 may have a tubular shape as shown in FIG. 5.

Each type of biodegradable polymer has a characteristic degradation rate in the body. Some materials are relatively fast-biodegrading materials (weeks to months) while others are relatively slow-biodegrading materials (months to years). The dissolution rate of baffle 50 may be tailored by controlling the type of biodegradable polymer, the thickness and/or density of the baffle 50, and/or the nature of the biodegradable polymer. Thus, increasing thickness and/or density of the baffle 50 slows the dissolution rate of the baffle 50 and reduces the rate at which the aperture 52 is opened. Characteristics such as the chemical composition and molecular weight of the biodegradable polymer may also be selected in order to control the dissolution rate of the baffle 50.

Figure 6:
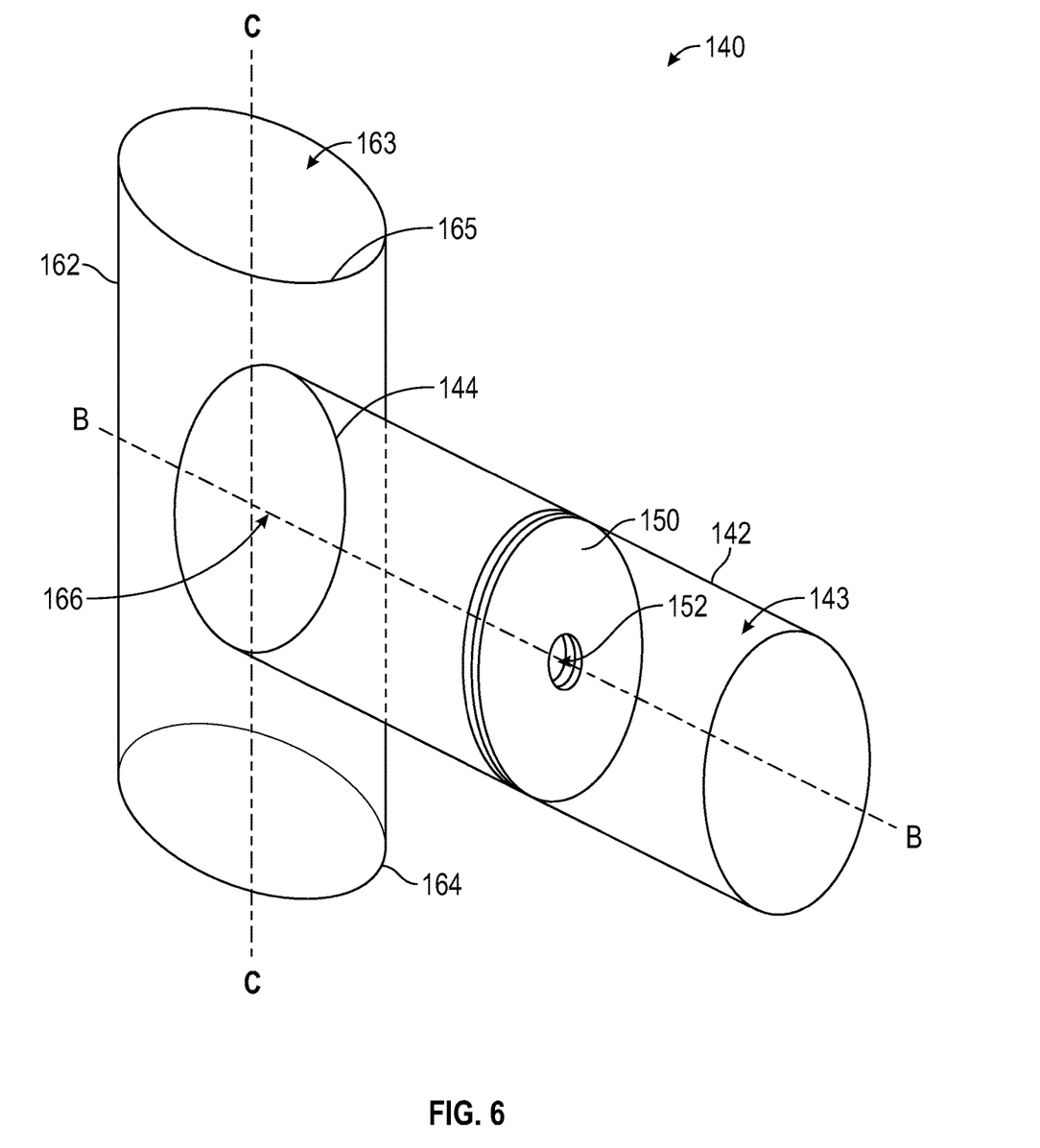
FIG. 6 is a perspective view of a medical implant for forming the AV fistula of FIG. 1 according to an embodiment of the present disclosure.

With reference to FIG. 6, a bifurcated medical implant 140 is shown, which is substantially similar to the medical implant 40 of FIG. 3. The bifurcated medical implant 140 is used to form the AV fistula 10. Accordingly, only the differences between the bifurcated medical implant 140 and the medical implant 40 are described below. The bifurcated medical implant 140 includes a first tubular member 142 and a second tubular member 162. The first tubular member 142 is substantially similar to the tubular member 42 of FIG. 3. The second tubular member 162 includes a first end portion 164, a second end portion 165, and a side opening 166 disposed at any location, e.g., mid-point, between the proximal end portion 164 and the distal end portion 165. The first and second tubular members 142 and 162 are joined in a "T" configuration, such that a proximal end portion 144 of the first tubular member 142 is coupled to the side opening 166 of the second tubular member 162. The first tubular member 142 defines a longitudinal axis "B-B" and a first lumen 143 therethrough and the second tubular member 162 defines a longitudinal axis "C-C" and a lumen 163 therethrough. In embodiments, the angle between the first and second tubular members 142 and 162, i.e., between axes "B-B" and "C-C" may be from about 10° to about 170° to accommodate various attachment configurations of the vein 12 and the artery 14. The first tubular member 142 is implanted in the artery 14 and the second tubular member 162 is implanted in the vein 12.

The bifurcated medical implant 140 also includes a baffle 150, which is substantially similar to the baffle 50. The baffle 150 is disposed within the first lumen 143 of the first tubular member 142, i.e., venous side, such that the baffle 150 modulates blood flow through the vein 12. The baffle 150 is substantially transverse to the longitudinal axis "B-B" such that blood flows only the through aperture 152.

Figure 7:
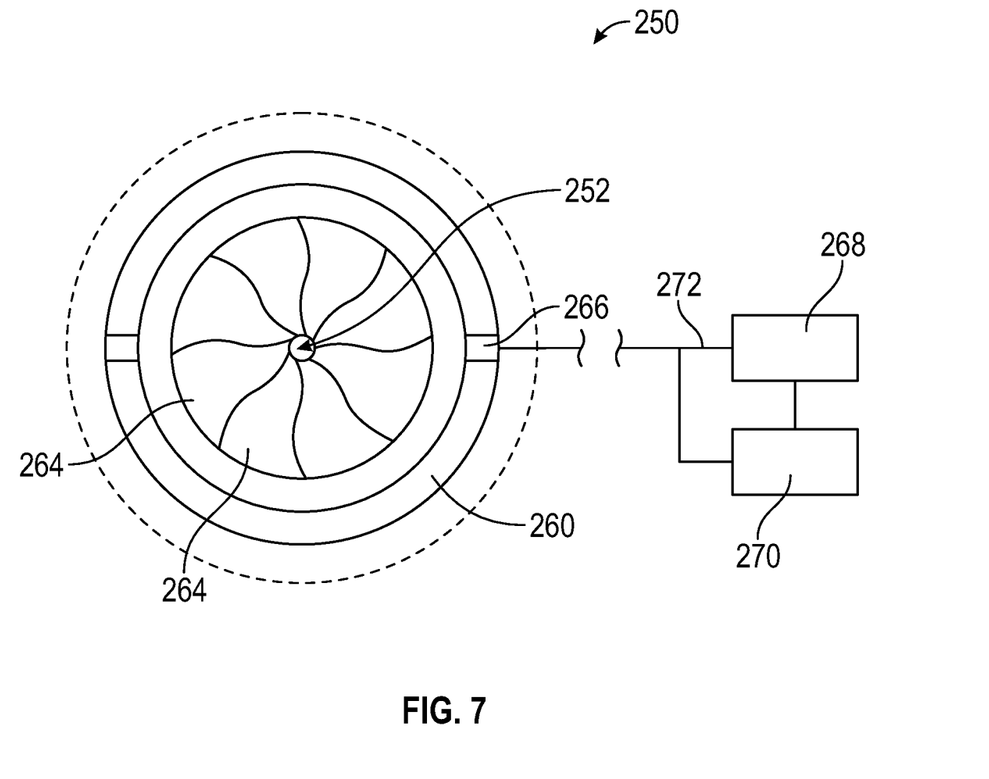
FIG. 7 is schematic view of an electromechanical baffle for use with the medical implants according to the present disclosure.

FIG. 7 shows another embodiment of a baffle 250, which includes an electromechanically adjustable aperture 252. The baffle 250 may be used in lieu of the baffle 50 and 150 within the medical implants 40 and 140. The baffle 250 includes an adjustable diaphragm 260 having a plurality of blades 264, which are radially rotatable, which allows for adjustment of the size of the aperture 252. The blades 264 may be actuated by one or more actuators 266, such as electromagnets activating permanent magnets (not shown) coupled to each of the blades 264. In embodiments, the actuator 266 may be an electrical motor mechanically coupled to each of the blades 264. The actuator 266 is coupled to a controller 268 and a power source 270, both of which are disposed outside the patient and are coupled to the actuator 266 via one or more leads 272. The controller 268 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The controller 268 controls the size of the aperture 252 by signaling the actuator 266 to actuate the blades 264 to a desired size of the aperture 252. The size of the aperture 252 may be automatically adjusted over time. The controller 268 may gradually adjust the size of the aperture 252 according to a preprogrammed schedule, such that at predetermined periods the size of the aperture 252 is increased until a desired size is achieved. In embodiments, the size of the aperture 252 may be manually adjusted by inputting the desired size into the controller 268, i.e., via a user interface (not shown).

With reference to FIGS. 1 and 2, showing the AV fistula 10 and the AV graft 20, an initial step in each of the procedures may include dissection and freeing up of the segments of the vein 12 and artery 14 identified for creation of the AV fistula 10 or the AV graft 20. Blood flow is stopped by clamping the targeted vein 12 and the artery 14. During this process, the vessels may be minimally disturbed in their in situ position while ligating and cutting off any small interfering side branches. The flush removal of all side branches may be performed. Minimal trauma dissection and freeing up of the vessel segments prevents any damage to the intimal layers of the vein 12 or artery 14 before insertion of the corresponding medical implant 40 or 140.

In forming the AV fistula 10 of FIG. 1, the anastomosis 16 is formed in the side 18 of the artery 14 and the first tubular member 142 of the medical implant 140 is inserted into the artery 14. Thereafter the vein 12 is inserted over the first tubular member 142. The vein 12 is then connected to the artery 14 using sutures. The medical implant 40 may be secured within the artery 14 and the vein 12 by the self-expanding nature of the medical implant 140 and/or using sutures. Once the AV fistula 10 is formed with the medical implant 140 disposed therein, blood flow is re-established, whereby the medical implant 140 limits the flow of blood into the vein 12. Overtime, as the baffle 150 is degraded, the size of the aperture(s) 152 increases, the blood flow increases, allowing the vein 12 to remodel and mature.

Forming the AV graft 20 of FIG. 2, includes forming the first anastomosis 22 in the vein 12 and the second anastomosis 24 in the artery 14. Thereafter the medical implant 40 is inserted into the grafted vessel 30 and secured therein. The grafted vessel 30 is then attached to the vein 12 and the artery 14. In particular, the first end 32 is sutured to the first anastomosis 22 of the vein 12 and the second end 34 is sutured to the second anastomosis 24 of the artery 14. Once the AV graft 20 is formed with the medical implant 40 disposed therein, blood flow is re-established, whereby the medical implant 40 limits the flow of blood into the vein 12. Overtime, as the baffle 50 is degraded, the size of the aperture(s) 52 increases, the blood flow increases, allowing the vein 12 to remodel and mature.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. A medical implant for controlling blood flow, the medical implant comprising:
    a primary tubular member having a first end and a second end and defining a primary longitudinal axis and a primary lumen, the primary tubular member disposed in an arterial-venous connection;
    a disk-like shaped baffle coupled to an interior surface of the tubular member, the baffle disposed transversely to the primary longitudinal axis within the primary lumen, the baffle defining a plurality of apertures therethrough, wherein the baffle is an electromechanical device configured to adjust at least one dimension of the plurality of apertures; and
    an adjustable diaphragm having a plurality of blades, which are radially rotatable to adjust a size of the plurality of apertures, wherein the plurality of blades are actuated by one or more actuators by an electromagnet activating permanent magnets coupled to each of the blades.

2. The medical implant of claim 1, wherein the plurality of apertures are frustoconical having a wider opening facing a direction of blood flow.

3. The medical implant of claim 1, wherein the plurality of apertures have a tubular shape.

4. The medical implant according to claim 1, wherein the arterial-venous connection is an arterial-venous fistula.

5. The medical implant according to claim 4, further comprising a secondary tubular member defining a secondary longitudinal axis and a secondary lumen, wherein the primary tubular member and the secondary tubular member are coupled to each other such that the first end of the primary tubular member is coupled to a side opening of the secondary tubular member.

6. The medical implant according to claim 5, wherein the primary tubular member and the secondary tubular member are transversely coupled to each other.

7. The medical implant according to claim 5, wherein an angle between the primary tubular member and the secondary tubular member is between 10° to 170°.

8. The medical implant according to claim 5, wherein the secondary tubular member is configured to be implanted in a vein.

9. The medical implant according to claim 1, wherein the arterial-venous connection is an arterial-venous graft including a graft vessel interconnecting an artery and a vein.

10. The medical implant according to claim 9, wherein the primary tubular member is disposed within the graft vessel.

11. The medical implant according to claim 9, wherein the primary tubular member is the graft vessel.

12. The medical implant according to claim 1, wherein the primary tubular member is a stent.

13. The medical implant according to claim 1, further including:
    a controller configured to control the size of the plurality of apertures by signaling the one or more actuators.

14. The medical implant according to claim 13, wherein the size of the plurality of apertures is automatically adjusted over time by the controller.

15. The medical implant according to claim 13, wherein the size of the plurality of apertures is adjusted according to a preprogrammed schedule.

16. The medical implant according to claim 13, wherein the size of the plurality of apertures is manually adjusted by inputting a desired size into the controller.

17. The medical implant according to claim 13, further including:
    a power source coupled to the one or more actuators via one or more leads.

18. The medical implant according to claim 13, wherein the one or more actuators is coupled to the controller via one or more leads.

19. The medical implant according to claim 1, wherein the disk-like shaped baffle is coupled to the interior surface of the tubular member using adhesives.

20. The medical implant according to claim 1, wherein the disk-like shaped baffle is coupled to the interior surface of the tubular member using mechanical fasteners.

* * * * *